United States Patent [19]

Zahn

[11] 4,112,742

[45] Sep. 12, 1978

[54] INSTRUMENT FOR MEASURING THE CONSISTENCY OF HIGH-CONSISTENCY MATERIALS

[76] Inventor: Edward A. Zahn, No. 2 San Remo Cir., Naples, Fla. 33940

[21] Appl. No.: 794,666

[22] Filed: May 6, 1977

[51] Int. Cl.² .................. G01N 11/00; G01N 33/26
[52] U.S. Cl. ................................................ 73/54
[58] Field of Search ................ 73/54, 150 R, 432 R, 73/169

[56] References Cited

U.S. PATENT DOCUMENTS

| 2,119,699 | 6/1938 | Bloom | 73/169 X |
| 3,631,712 | 1/1972 | Mercier | 73/54 |

FOREIGN PATENT DOCUMENTS 466,653 10/1928 Fed. Rep. of Germany ............. 73/54

OTHER PUBLICATIONS

*Testing Instruments for the Paint and Other Industries,* Gardner Laboratory, Inc. Dec. 1950, pp. 30–31.

Primary Examiner—Richard C. Queisser
Assistant Examiner—Joseph W. Roskos
Attorney, Agent, or Firm—Burns, Doane, Swecker & Mathis

[57] ABSTRACT

An instrument for measuring the consistency of high-consistency materials such as heavy liquids, semi-liquids, and semi-pastes which comprises a tube section flared at the bottom which is immersed vertically into a volume of the material until it has been completely covered and the inside completely filled. The tube is then withdrawn slowly and the amount of the material retained on the entire surface of the tube at the end of the drip cycle following its withdrawal is a measure of its consistency and this is weighed by means of a scale attached to the tube by a bale type handle on the tube, the latter also facilitating immersion of the tube.

4 Claims, 4 Drawing Figures

INSTRUMENT FOR MEASURING THE CONSISTENCY OF HIGH-CONSISTENCY MATERIALS

BACKGROUND OF THE INVENTION

The present invention relates to a new and improved instrument which I have termed a "liquid consistency meter" designed for highly accurate measurement of the consistency of heavy liquids, semi-liquids, or semi-paste compositions. One practical and specific example of use of the improved instrument is for measuring high-consistency, water-based latex paints but is by no means limited to such an application. The instrument is capable of measuring extremely thick compositions with complete accuracy and all measurements are accurately reproducible. It can measure unthinned as well as thinned compositions. Heavy liquids, water or solvent based, even those with fibrous fillers added, or even those with small lumps can be accurately measured. Also asphalt or gilsonite heavy mixtures. The instrument is also useful for measuring ceramic frit mixtures, slurries, etc. Semi-liquid heavy oils and greases, or typical roof coatings, both water and solvent based, with or without fibrous additions can also be measured accurately. The instrument is also useful in the food industry in connection with processing of batters, sauces, ketchup, and the like. Other possible uses for the instrument are for measurement of the consistency of semi-liquid pigment pastes, resin solutions, semi-liquid printing ink pastes and other similar materials.

The instrument in accordance with the invention is not intended as a substitute for conventional flow viscosity measurements. Rather it is intended as a means for measuring compositions which have a high consistency beyond the normal scope of flow viscosity, e.g., in cases where flow viscosity measurements become ineffective due to the capillary and consistency differences between solvent-based and water-based mixtures.

To my knowledge, none of the 20 to 30 flow or eflux types of viscometers, including the well known "Zahn Cups" is capable of measuring the consistency of extremely heavy liquids, for example, unthinned latex paints, because a thixotropic condition, or false body, or both, exist in the latex paints as produced. Even though most of the latex paints now being marketed contain 50% of more of water, the consistency is so high that the material cannot flow through an orifice of normal size. Often, thickening agents are added to increase the thickness factor to a point where pigment settling cannot occur and this also prevents drips or runs when the material is applied to a substrate by conventional means.

Some rather elaborate and hence expensive viscosity measuring devices are known which can measure the liquid shear resistance of heavy liquids, e.g., U.S. Pat. No. 3,569,722 — Denson — granted Mar. 9, 1971, but such measurements have no relationship to my invention in the consistency meter to be described hereinafter in more detail. Shear-resistance of a heavy liquid, for the most part, is a direct result of the material's (nonvolatile) content. A relatively thin material with a high pigment content can exhibit high shear resistance. In a certain sense, these instruments are affected by the element of viscosity, but by including the shear resistance as principal factor, they in no way indicate the actual viscosity of the material being measured.

SUMMARY OF THE INVENTION

The consistency instrument, or meter in accordance with my invention measures the consistency of heavy liquids, semi-liquids, or semi-paste compositions as a function of the volume of the composition which will cling to the surface of a tube section, flared at the bottom, which is immersed vertically into the composition until completely covered and the inside of the tube is completely filled, and is then slowly lifted from the latter by a movement in a vertically upward direction. The amount of the composition clinging to the internal, external, bottom and top horizontal surfaces is proportional to its consistency and this is weighed by attaching a scale, e.g., a dial reading type, to the immersion tube, scale being calibrated for example in grams. The gram weight of the tube and a bale type handle for it are subtracted from the total gram weight load. The remaining gram weight which I call "ZG's" (Zahn Grams) is the "consistency" of the composition. I have found that with the use of my improved instrument, as little as 5 cc's of water added to a quart of conventional latex paint can change the reading by as much as 3 ZG's.

BRIEF DESCRIPTION OF THE DRAWINGS

A preferred embodiment of the consistency measuring instrument in accordance with my invention will be described below in detail and is illustrated in the accompanying drawings wherein.

DETAILED DESCRIPTION OF PREFERRED EMBODIMENT

Figure 1:
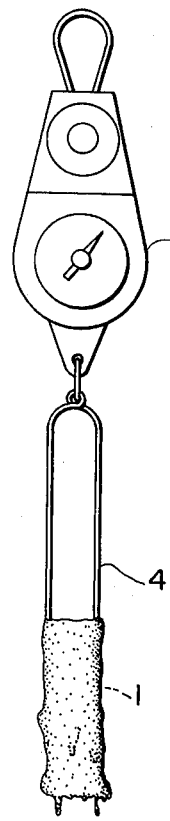
FIG. 1 is a view in elevation of the immersion tube with bale attached and there being a scale attached to the bale for weighing the combined weight of the tube, bale, and material clinging to all surfaces of the tube upon withdrawal from a container.
Figure 2:
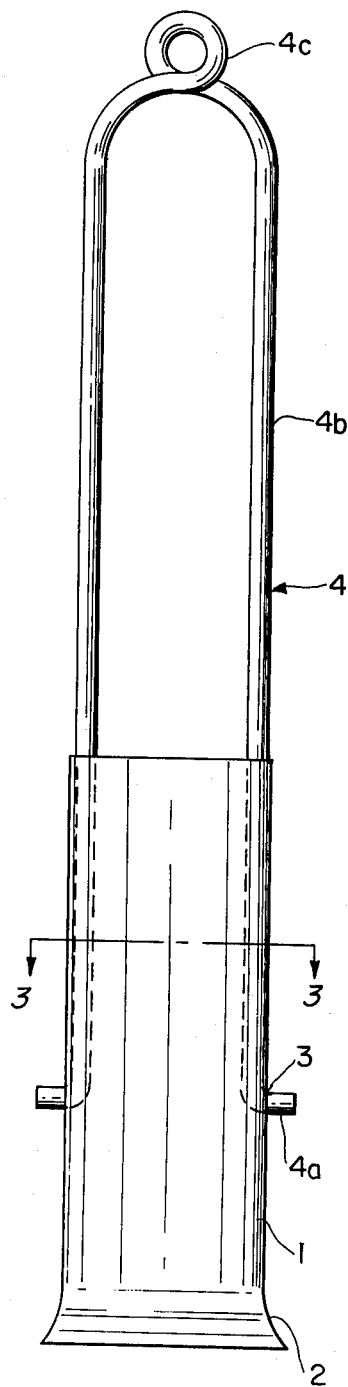
FIG. 2 is a view in side elevation of the immersion tube itself.
Figure 4:
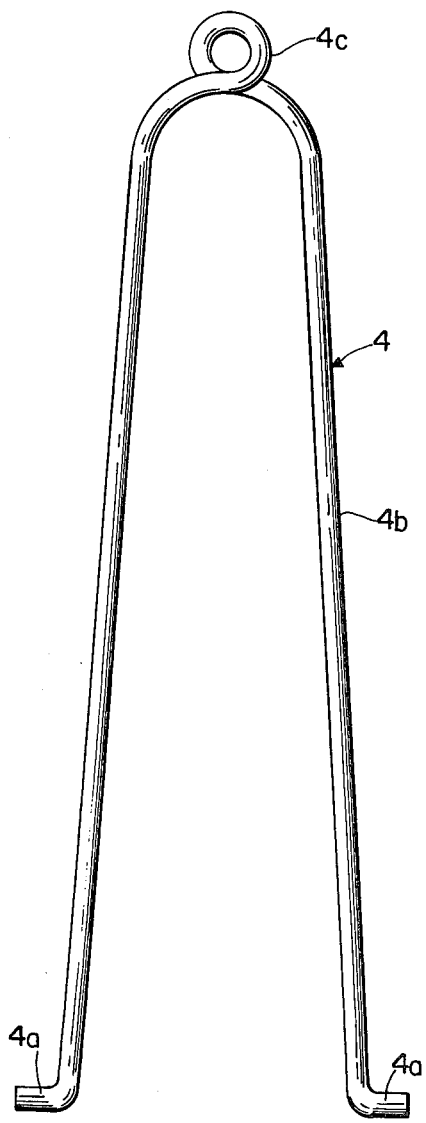
FIG. 4 is a view of the spring-type bale in its relaxed unsprung state.
Figure 3:
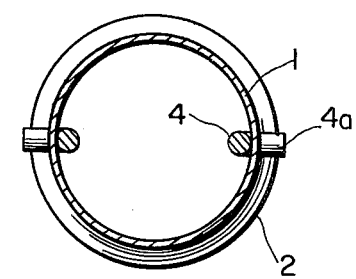
FIG. 3 is a transverse section through the tube taken on line 3 — 3 of FIG. 2.

With reference now to the drawings, the immersion tube 1 in particular which is made with fine tolerances and with computer accuracy is made from light-weight aluminum and is extruded, seamless, factory polished, and of a hardness number which can be flared at the bottom without cracking to provide a flared surface 2. The function served by the flared bottom end 2 is to prevent the material from sliding or slipping off the bottom of the tube. Although its specific dimensions can be altered, in one suitable construction, the tube has a length of 3¾ inches, a wall thickness of 0.049 inch, and internal diameter of 1¼ inches and a diameter of 1¾ inches at the bottom of the flare which measures ¼ inch.

Two 5/32 inch holes 3 are provided in the tube opposite one another at a distance of 2¼ inches below the top which receive the lower, outwardly turned ends 4a of an inverted U-shaped bale 4 made from ⅛ inch diameter hard, aluminum wire in order to reduce the weight of the immersion tube and bale to a minimum since the instrument will be operated in accordance with fractions of gram weight. The overall length of the bale is 7 inches. The bale has an inherent spring characteristic due to its hardness and configuration and thus retains its out-turned ends 4a securely within the holes 3 and its straight legs 4b in contact with the internal surface of tube 1. However, if desired, and as illustrated, the bale may also include a loop 4c at the top which not only increases its springiness but also provides an eye for attachment to the hook 5a of scale 5.

The spring-loaded connection between the ends of the bale and tube enable the two components to be easily separated and assembled which facilitates cleaning of the instrument after use.

Location of the holes 3 below the center of the length of tube 1 is advantageous since it permits the tube with bale 4 attached to be pushed downward into the heavy liquid or other material the consistency of which is desired to be measured without producing any undesirable tilt action on the tube.

The total surface of the immersion tube 1, plus the immersible portion of the wire bale 4, minus the surface area of the two holes 3 for the bale is designed to be equal to a total of 30 square inches of surface. This will then permit expression of consistency measurement in terms of ZG's (Zahn Grams) per square inch, if desired. For example, a normal latex paint from the shelf could show a reading of 1 ZG per square inch consistency or, it could be simply expressed as 30 ZG's consistency.

To use the instrument, the assembled tube 1 and bale 4 are pushed down into the high consistency material in container 6 to be measured until the top edge of the tube is covered and the inside of the tube is full. The dial-pointed type scale 5 in which has been pre-adjusted to zero reading with the tube and the bale attached, is then connected to the bale 4 and the tube is withdrawn slowly from the material. As soon as the drip stops (the drip time for heavier liquids is practically zero) the consistency is then read directly from the scale dial 5a. Following use, the scale is detached, bale 4 is removed from tube 1 and the latter two components are immersed in a suitable solvent or water for clean-off.

Since liquid consistency is lowered by thinning, the drip time of the liquid is of course lengthened. Thus, as indicated above, the reading on scale 5 should be taken immediately at the end of the drip cycle and which is relatively short. If desired, further information concerning the consistency of the material can be obtained by the use of a stop-watch to time the drip cycle which changes with varying reductions in consistency. Stop-watch readings can also be taken before and after the drip cycle to further determine the effect of thinning. The resulting reading is then in ZG's versus seconds.

I claim:

1. An instrument for measuring the consistency of high-consistency materials comprising a cylindrical tube which is flared at one end and an inverted springy U-shaped bale the legs of which terminate in turned end portions and engage diametrically spaced holes through the tube wall at a distance from the flared end less than one half the length of the tube, said bale serving to assist complete immersion into and withdrawal from a volume of the material to be measured, the amount of the material retained on the entire surface of said tube at the end of the drip cycle following its withdrawal being a measure of its consistency.

2. An instrument as defined in claim 1 for measuring the consistency of high-consistency materials wherein said tube is made from a hard, polished and relatively thin aluminum.

3. An instrument as defined in claim 1 for measuring the consistency of high-consistency materials wherein said U-shaped bale is made from hard aluminum to develop a springy characteristic.

4. An instrument as defined in claim 1 for measuring the consistency of high-consistency materials and which further includes a scale connectible to said bale for weighing the amount of the material retained on the entire surface of said tube at the end of the drip cycle following its withdrawal.

* * * * *